(12) United States Patent
Denney et al.

(10) Patent No.: US 6,274,616 B1
(45) Date of Patent: Aug. 14, 2001

(54) N,N-DIETHYLGLYCOLAMIDO ESTER PRODRUGS OF INDOLE SPLA2 INHIBITORS

(75) Inventors: Michael L Denney, Franklin; John M Morin, Jr., Brownsburg; Daniel J Sall, Greenwood; Jason S Sawyer, Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/509,754

(22) Filed: Mar. 29, 2000

Related U.S. Application Data

(63) Continuation of application No. PCT/US98/22690, filed on Oct. 26, 1998.
(60) Provisional application No. 60/063,280, filed on Oct. 27, 1997.

(51) Int. Cl.$^7$ ................................................ A61K 31/40
(52) U.S. Cl. ........................................................ 514/419
(58) Field of Search .............................................. 514/419

(56) References Cited

U.S. PATENT DOCUMENTS

| | | | | |
|---|---|---|---|---|
| 5,641,800 | * | 6/1997 | Bach et al. ........................... | 514/415 |
| 5,654,326 | * | 8/1997 | Bach et al. ........................... | 514/419 |

* cited by examiner

*Primary Examiner*—James H. Reamer
(74) *Attorney, Agent, or Firm*—Roger S. Benjamin

(57) ABSTRACT

The compound, ((3-(2-amino-1,2-dioxoethyl)-1-((1,1'-biphenyl-3-ylmethyl)-2-methyl-1H-indol-4-yl)oxy)acetic acid N,N-diethylglycolamido ester, is disclosed together with its use as a highly bioavailable indole compound for inhibiting sPLA$_2$ mediated release of fatty acids for treatment of conditions such as septic shock.

6 Claims, No Drawings

N,N-DIETHYLGLYCOLAMIDO ESTER PRODRUGS OF INDOLE SPLA2 INHIBITORS

This application is a 371 of PCT/US98/22690 filed Oct. 26, 1998 which, claims benefit to Provisional Application No. 60/063280 filed Oct. 27, 1997.

FIELD OF THE INVENTION

This invention relates to a novel prodrug form of $sPLA_2$ inhibitor having exceptionally high bioavailability.

BACKGROUND OF THE INVENTION

The structure and physical properties of human non-pancreatic secretory phospholipase $A_2$ (hereinafter called, "$sPLA_2$") has been thoroughly described in two articles, namely, "Cloning and Recombinant Expression of Phospholipase $A_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase $A_2$," by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

It is believed that $sPLA_2$ is a rate limiting enzyme in the arachidonic acid cascade which hydrolyzes membrane phospholipids. Thus, it is important to develop compounds which inhibit $sPLA_2$ mediated release of fatty acids (e.g., arachidonic acid) and are highly bioavailable in mammals, especially humans. Such compounds are of value in general treatment of conditions induced and/or maintained by overproduction of $sPLA_2$; such as septic shock, adult respiratory distress syndrome, pancreatitis, trauma, bronchial asthma, allergic rhinitis, rheumatoid arthritis, etc.

Therapeutic agents that may be given orally are, in general, greatly preferred and have enhanced commercial potential because of their inherent ease of use.

Glycolamide esters as prodrugs are described in the chemical literature, for example; (1) "Evaluation of Glycolamide Esters and Various Other Esters of Aspirin as True Aspirin Prodrugs" by Niels Mork Nielsen and Hans Bundgaard, J. Med. Chem. 1989, Vol. 32, pp. 727–734; and (2) "Glycolamide Esters as Biolabile Prodrugs of Carboxylic Acid Agents: Synthesis, Stability, Bioconversion, and Physicochemical Properties" by Niels Mork Nielsen and Hans Bundgaard, Journal of Pharmaceutical Sciences, Vol. 77, No. 4, April 1988.

U.S. Pat. No. 5,654,326 describes certain indole type $sPLA_2$ inhibitors. In particular, this patent exemplifies the methyl ester of ((3-(2-amino-1,2-dioxoethyl)-1-((1,1'-biphenyl)-3-ylmethyl)-2-methyl-1H-indol-4-yl)oxy)acetic acid.

It is desirable to develop more highly available $sPLA_2$ inhibitors, particularly those suitable for oral administration.

SUMMARY OF THE INVENTION

This invention is the novel compound, ((3-(2-amino-1,2-dioxoethyl)-1-((1,1'-biphenyl)-3-ylmethyl)-2-methyl-1H-indol-4-yl)oxy)acetic acid N,N-diethylglycolamido ester; which is highly bioavailable by oral administration.

This invention is also a pharmaceutical formulation containing the novel compound of the invention.

This invention is also a method of inhibiting $sPLA_2$ mediated release of fatty acid by contacting $sPLA_2$ with the novel compound of the invention.

DETAILED DESCRIPTION OF THE INVENTION

The 1H-indole-3-glyoxylamide Compound of the Invention

The compound of the invention((3-(2-amino-1,2-dioxoethyl)-1-((1,1'-biphenyl)-3-ylmethyl)-2-methyl-1H-indol-4-yl)oxy)acetic acid N,N-diethylglycolamido ester; is represented by the structural formula (I);

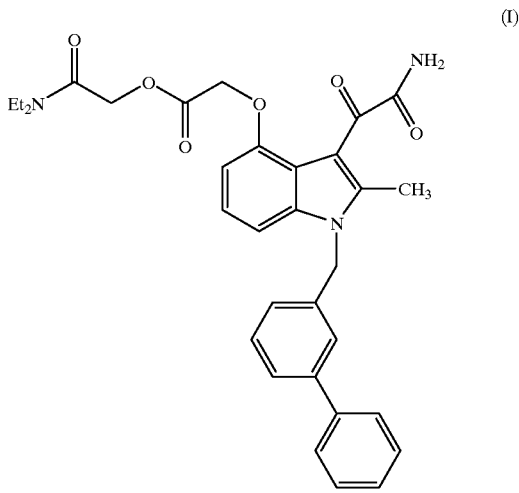

The N,N-diethylglycolamido ester (I) is an ester form of known $sPLA_2$ inhibitor ((3-(2-amino-1,2-dioxoethyl)-1-((1,1'-biphenyl)-3-ylmethyl)-2-methyl-1H-indol-4-yl)oxy) acetic acid, represented by the structural formula (II), below;

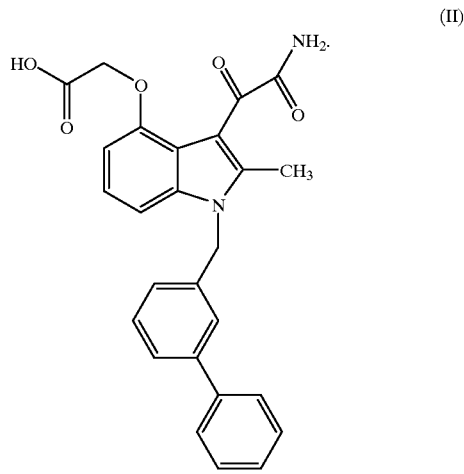

The compound of formula (II) is described in Example 4 of U.S. Pat. No. 5,654,326 (the disclosure of which is incorporated herein by reference) and European Patent Application No. 95302166.4, Publication No. 0 675 110 (publ., Oct. 4, 1995).

Prodrugs are derivatives of therapeutic agents which have chemically or metabolically cleavable groups and become under physiological conditions known compounds of therapeutic effectiveness.

It is a discovery of this invention that the compound of formula (I) is highly bioavailable upon oral administration compared to other common ester type prodrugs.

Synthesis of the Compound of the Invention

The synthesis of ((3-(2-amino-1,2-dioxoethyl)-1-((1,1'-biphenyl)-3-ylmethyl)-2-methyl-1H-indol-4-yl)oxy)acetic acid N,N-diethylglycolamido ester (compound of formula I, supra.) uses as starting material ((3-(2-amino-1,2-dioxoethyl)-1-((1,1'-biphenyl)-3-ylmethyl)-2-methyl-1H-indol-4-yl)oxy)acetic acid, or a salt thereof (compound of formula II, supra.). This starting material may be prepared by the reaction schemes or method of Example 4 of U.S. Pat. No. 5,654,326 (the disclosure of which is incorporated herein by reference). Similar methods are shown in European Patent Application No. 95302166.4, Publication No. 0 675 110 (publ., Oct. 4, 1995). Other methods well known and recorded in the chemical literature may also be used for preparing the starting material. Procedures useful for the synthesis of the starting material are shown in both Scheme 1 and Example 1 set out below:

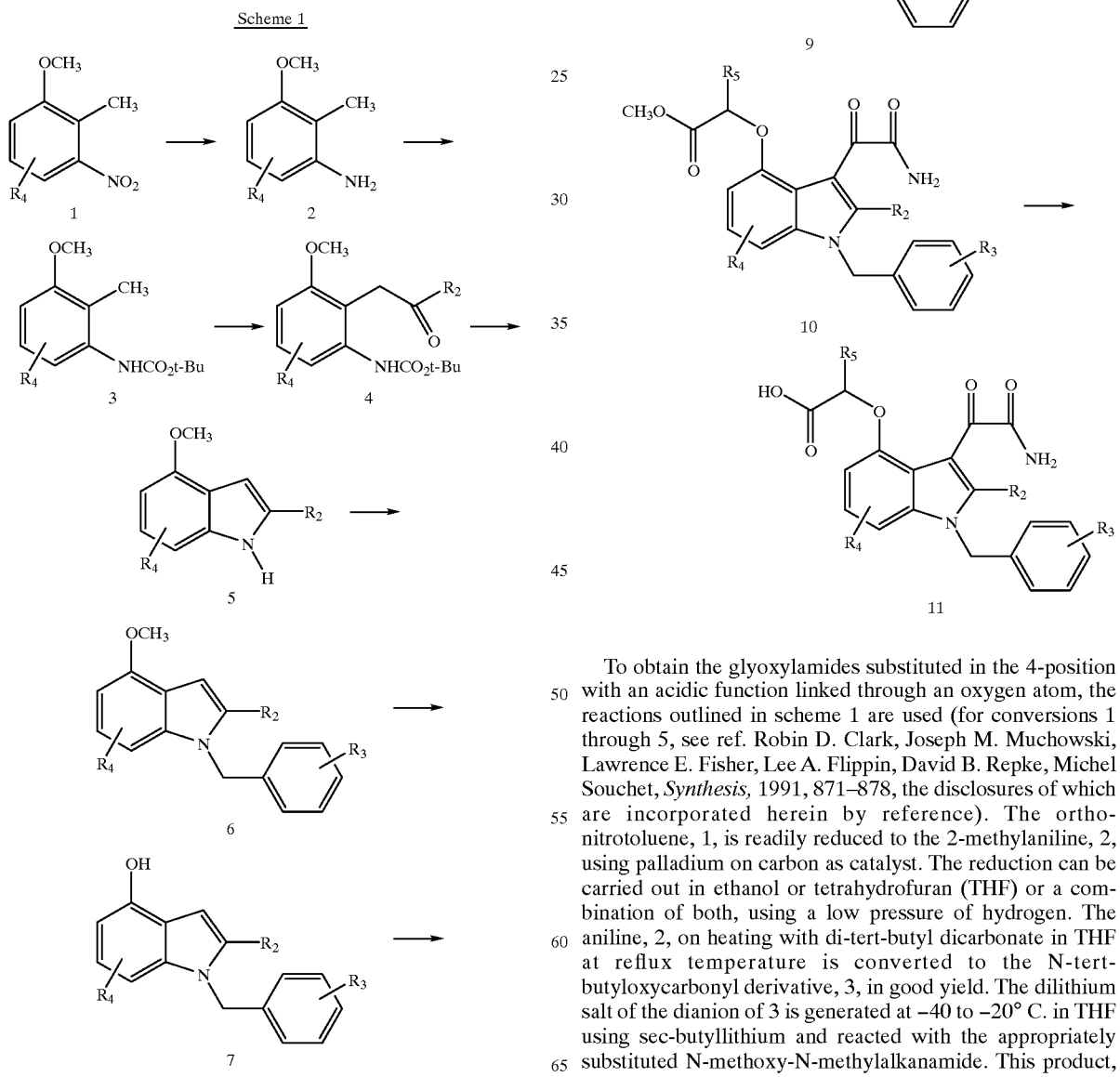

To obtain the glyoxylamides substituted in the 4-position with an acidic function linked through an oxygen atom, the reactions outlined in scheme 1 are used (for conversions 1 through 5, see ref. Robin D. Clark, Joseph M. Muchowski, Lawrence E. Fisher, Lee A. Flippin, David B. Repke, Michel Souchet, *Synthesis,* 1991, 871–878, the disclosures of which are incorporated herein by reference). The ortho-nitrotoluene, 1, is readily reduced to the 2-methylaniline, 2, using palladium on carbon as catalyst. The reduction can be carried out in ethanol or tetrahydrofuran (THF) or a combination of both, using a low pressure of hydrogen. The aniline, 2, on heating with di-tert-butyl dicarbonate in THF at reflux temperature is converted to the N-tert-butyloxycarbonyl derivative, 3, in good yield. The dilithium salt of the dianion of 3 is generated at −40 to −20° C. in THF using sec-butyllithium and reacted with the appropriately substituted N-methoxy-N-methylalkanamide. This product, 4, may be purified by crystallization from hexane, or reacted directly with trifluoroacetic acid in methylene chloride to give the 1,3-unsubstituted indole 5. The 1,3-unsubstituted indole 5 is reacted with sodium hydride in dimethylformamide at room temperature (20–25° C.) for 0.5–1.0 hour. The resulting sodium salt of 5 is treated with an equivalent of arylmethyl halide and the mixture stirred at a temperature range of 0–100° C., usually at ambient room temperature, for a period of 4 to 36 hours to give the 1-arylmethylindole, 6. This indole, 6, is O-demethylated by stirring with boron tribromide in methylene chloride for approximately 5 hours (see ref. Tsung-Ying Shem and Charles A Winter, *Adv. Drug Res.*, 1977, 12, 176, the disclosure of which is incorporated herein by reference). The 4-hydroxyindole, 7, is alkylated with an alpha bromoalkanoic acid ester in dimethylformamide (DMF) using sodium hydride as a base, with reactions conditions similar to that described for the conversion of 5 to 6. The α-((indol-4-yl)oxy)alkanoic acid ester, 8, is reacted with oxalyl chloride in methylene chloride to give 9, which is not purified but reacted directly with ammonia to give the glyoxamide 10. This product is hydrolyzed using 1N sodium hydroxide in methanol. The final glyoxylamide, 11, is isolated either as the free carboxylic acid or as its sodium salt or in both forms.

EXAMPLE 1

Method of Preparing ((3-(2-amino-1,2-dioxoethyl)-1-((1,1'-biphenyl)-3-ylmethyl)-2-methyl-1H-indol-4-yl)oxy)acetic acid Part A. Preparation of 1-((1,1'-biphenyl)-3-ylmethyl)-2-methyl-4-methoxy-1H-indole 805 mg (5 mmol) of 4-methoxy-2-methyl-1H-indole is reacted with 200 mg (5 mmol) of 60% NaH/mineral oil (washing with hexane before adding DMF) in 15 mL of DMF and after stirring for 0.5 hour, 1.0 g (5 mmol) of 3-(chloromethyl)biphenyl is added. The mixture is stirred at room temperature for 18 hours, diluted with water and extracted with ethyl acetate. The ethyl acetate solution is washed with brine, dried ($MgSO_4$) and after concentrating at reduced pressure, the residue is chromatographed on silica gel eluting with 20% EtOAc/hexane to give 1.25 g (76% yield) of 1-((1,1'-biphenyl)-3-ylmethyl)-2-methyl-4-methoxy-1H-indole mp, 127°–131° C.

Part B. Preparation of 1-((1,1'-biphenyl)-3-ylmethyl)-2-methyl-4-hydroxy-1H-indole A solution of 125 mg (3.8 mmol) of 1-((1,1'-biphenyl)-3-ylmethyl)-2-methyl-4-methoxy-1H-indole is O-demethylated by treating it with 15 mL of 1M $BBr_3$/$CH_2Cl_2$. The reaction mixture is stirred at room temperature for 5 hours and concentrated at reduced pressure. The crude product is chromatographed on silica gel and is eluted with 20% EtOAc/hexane to give 1030 mg (87% yield) of 1-((1,1'-biphenyl)-3-ylmethyl)-2-methyl-4-hydroxy-1-indole.

Part C. Preparation of ((1-((1,1'-biphenyl)-3-ylmethyl)-2-methyl-1H-indol-4-yl)oxy)acetic acid methyl ester 1-((1,1'-Biphenyl)-3-ylmethyl)-4-hydroxy-2-methyl-1H-indole (1030 mg, 3.3 mmol) is alkylated by treating with 0.31 mL (3.3 mmol) of methyl bromoacetate and 132 mg (3.3 mmol) and 132 mg (3.3 mmol) of 60% NaH/mineral oil in DMF and stirring maintained for about 17 hours. The mixture is diluted with water and extracted with ethyl acetate. The ethyl acetate solution is washed with brine, dried ($MgSO_4$), and concentrated at reduced pressure. The product is purified by chromatography over silica gel eluting with 20% EtOAc/hexane, to give 1000 mg (79% yield) of ((1-((1,1'-biphenyl)-3-ylmethyl)-2-methyl-1H-indol-4-yl)oxy)acetic acid methyl ester; mp 99°–102° C.

Part D. Preparation of ((3-(2-amino-1,2-dioxoethyl)-1-((1,1'-biphenyl)-3-ylmethyl)-2-methyl-1H-indol-4-yl)oxy)acetic acid methyl ester.

Oxalyl chloride (0.23 mL, 2.6 mmol) is added to 1000 mg (2.6 mmol) of ((1-((1,1'-biphenyl)-3-ylmethyl)-2-methyl-1H-indole-4-yl)oxy)acetic acid methyl ester in 15 mL of methylene chloride and the mixture is stirred for 1.3 hours at room temperature. The mixture is concentrated at reduced pressure, the residue redissolved in 15 mL of methylene chloride, ammonia bubbled in for 0.25 hours, stirred for 0.25 hours and concentrated. The residue is stirred with EtOAc/water and the undissolved material filtered to give 300 mg of ((3-(2-amino-1,2-dioxoethyl)-1-((1,1'-biphenyl)-3-ylmethyl)-2-methyl-1H-indol-4-yl)oxy)acetic acid methyl ester. The residue was chromatographed on silica gel eluting with EtOAc to give an additional 671 mg of product. mp, 175°–179° C. The total combined yield of product was 82%.

Part E. Preparation of ((3-(2-amino-1,2-dioxoethyl)-1-((1,1'-biphenyl)-3-ylmethyl)-2-methyl-1H-indol-4-yl)oxy)acetic acid A mixture of 956 mg (2.1 mmol) of ((3-(2-amino-1,2-dioxoethyl)-1-((1,1'-biphenyl)-3-ylmethyl)-2-methyl-1H-indol-4-yl)oxy)acetic acid methyl ester is hydrolyzed at reflux in 10 mL of 1N NaOH and 20 mL of MeOH to give 403 mg (41% yield) of ((3-(2-amino-1,2-dioxoethyl)-1-((1,1'-biphenyl)-3-ylmethyl)-2-methyl-1H-indol-4-yl)oxy) acetic acid, sodium salt, mp, greater than 265° C.

Analyses for $C_{26}H_{21}N_2O_5Na$:

Calculated: C, 67.24; H, 4.56; N, 6.03.

Found: C, 67.20; H, 4.58; N, 6.03.

There is also obtained 346 mg (37% yield) of ((3-(2-amino-1,2-dioxoethyl)-1-((1,1'-biphenyl)-3-ylmethyl)-2-methyl-1H-indol-4-yl)oxy)acetic acid, mp, 236°–238° C.

Analyses for $C_{26}H_{22}N_2O_5$:

Calculated: C, 70.58; H, 5.01; N, 6.33.

Found: C, 70.58; H, 5.25; N, 6.11.

Beginning with the indole starting material of formula (II) prepared by the above methods the ((3-(2-amino-1,2-dioxoethyl)-1-((1,1'-biphenyl)-3-ylmethyl) -2-methyl-1H-indole-4-yl)oxy)acetic acid N,N-diethylglycolamido ester compound of the invention is prepared by esterification of the acid or salt form of the starting material. Any ester forming method which is conventional in the chemical arts may be used. A suitable procedure used to prepare the compound of the invention is as follows:

EXAMPLE 2

Preparation of ((3-(2-amino-1,2-dioxoethyl)-1-((1, 1'-biphenyl)-3-ylmethyl)-2-methyl-1H-indol-4-yl) oxy)acetic acid N,N-diethylglycolamido ester In a flask containing 10 ml of dimethylformamide was added with stirring 0.1 ml of 2-chloro-N,N-diethylacetamide (available from Aldrich Chemical Co., Milwaukee, Wis. USA; Item No. 25,099-6) and 300 mg. of ((3-(2-amino-1, 2-dioxoethyl)-1-((1,1'-biphenyl)-3-ylmethyl)-2-methyl-1H-indole-4-yl)oxy)acetic acid, sodium salt. The slurry was heated to 60° C. until a solution formed. Heating was continued overnight until reaction was complete. The following morning the reaction mixture was poured into 50 ml of saturated NaHCO$_3$, then extracted with ethyl acetate. The ethyl acetate solution was washed with water, dried over Na$_2$SO$_4$ and concentrated at reduced pressure. The title compound is crystallized from EtoAc/hexane.

Molecular Formula: C$_{32}$H$_{33}$N$_3$O$_6$

Calculated % C=69.17; H=6.51; N=7.56.

Found % C=68.73; H=5.88; N=7.40.

Formulations Suitable for Use in the Method of the Invention

The sPLA$_2$ inhibitor of formula (I) used in the method of the invention is administered so as to make contact with sPLA$_2$ in the body of the mammal being treated.

The preferred route of administration for the compound of this invention is orally, either as neat compound or as the active compound in a pharmaceutical formulation.

The sPLA$_2$ inhibitor can be administered alone, but is generally administered with a pharmaceutical carrier or diluent selected on the basis of the chosen route of administration and standard pharmaceutical practice.

By "pharmaceutically acceptable" it is meant the carrier, diluent or excipient must be compatible with the formula (II) sPLA$_2$ inhibitor ("active compound") in the formulation and not deleterious to the subject being treated.

For the pharmaceutical formulations any suitable carrier known in the art can be used. In such a formulation, the carrier may be a solid, liquid, or mixture of a solid and a liquid. A solid carrier can be one or more substances which may also act as flavoring agents, lubricants, solubilizers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. In tablets the sPLA$_2$ inhibitor is mixed with a carrier having the necessary binding properties in suitable proportions and compacted in the shape and size desired.

Sterile liquid form formulations include suspensions, emulsions, syrups and elixirs. The active compound can be dissolved or suspended in a pharmaceutically acceptable carrier, such as sterile water, saline, dextrose solution, sterile organic solvent or a mixture of both.

The active compound can be administered orally in solid dosage forms, such as capsules, tablets, and powders, or in liquid dosage forms, such as elixirs, syrups, and suspensions. It can also be administered parenterally, in sterile liquid dosage forms. It can also be administered by inhalation in the form of a nasal spray or lung inhaler. It can also be administered topically as an ointment, cream, gel, paste, lotion, solution, spray, aerosol, liposome, or patch. Dosage forms used to administer the active compound usually contain suitable carriers, diluents, preservatives, or other excipients, as described in Remington's Pharmaceutical Sciences, Mack Publishing Company, a standard reference text in the field.

Gelatin capsules may be prepared containing the active compound and powdered carriers, such as lactose, sucrose, mannitol, starch, cellulose derivatives, magnesium stearate, stearic acid, and the like. Similar diluents can be used to make compressed tablets and powders. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For parenteral solutions, water, a suitable oil, saline, aqueous dextrose (glucose), and related sugar solutions and glycols such as propylene glycol or polyethylene glycols are suitable carriers for parenteral solutions. Solutions for parenteral administration contain the active compound, suitable stabilizing agents, and if necessary, buffer substances. Anti-oxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Formulations within the scope of this invention include the admixture of sPLA$_2$ inhibitor with a therapeutically effective amount of any therapeutically effective co-agents, such as other sPLA2 inhibitors, leukotriene antagonists or cycloxygenase inhibitors for treating the disease target.

Proportion and Weight of Active Compounds Used in the Method of the Invention

The compound of formula (I) may be used at a concentration of 0.1 to 99.9 weight percent of the pharmaceutical formulation.

Preferably the pharmaceutical formulation is in unit dosage form. The unit dosage form can be a capsule or tablet itself, or the appropriate number of any of these. The quantity of active compound in a unit dose of composition may be varied or adjusted from about 0.1 to about 1000 milligrams or more according to the particular treatment involved.

Compositions (dosage forms) suitable for internal administration contain from about 1 milligram to about 500 milligrams of active compound per unit.

Examples of useful pharmaceutical compositions and their proportions of ingredients are illustrated as follows:

Capsules: Capsules may be prepared by filling standard two-piece hard gelatin capsules each with 50 mg of powdered active compound, 175 mg of lactose, 24 mg of talc, and 6 mg of magnesium stearate.

Soft Gelatin Capsules: A mixture of active compound in soybean oil is prepared and injected by means of a positive displacement pump into gelatin to form soft gelatin capsules containing 50 mg of the active compound. The capsules are washed in petroleum ether and dried.

Tablets: Tablets may be prepared by conventional procedures so that the dosage unit is 50 mg of active compound, 6 mg of magnesium stearate, 70 mg of microcrystalline cellulose, 11 mg of cornstarch, and 225 mg of lactose. Appropriate coatings may be applied to increase palatability or delay absorption. Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. The tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Suspensions: An aqueous suspension is prepared for oral administration so that each 5 ml contain 25 mg of finely divided active compound, 200 mg of sodium carboxymethyl cellulose, 5 mg of sodium benzoate, 1.0 g of sorbitol solution, U.S.P., and 0.025 mg of vanillin.

Injectables: A parenteral composition suitable for administration by injection is prepared by stirring 1.5% by weight of active compound in 10% by volume propylene glycol and water. The solution is sterilized by commonly used techniques.

Nasal Spray: An aqueous solution is prepared such that each 1 ml contains 10 mg of active compound, 1.8 mg methylparaben, 0.2 mg propylparaben and 10 mg methylcellulose. The solution is dispensed into 1 ml vials. The active compound may be used at a concentration of 0.1 to 99.9 weight percent of the formulation.

Aerosol formulations are capable of dispersing into particle sizes of from about 0.5 to about 10 microns and have sufficient $sPLA_2$ inhibitor to achieve concentrations of the inhibitor on the airway surfaces of from about $10^{-10}$ to $10^{-2}$ moles per liter.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active compound can be about 0.1 to 200 milligrams per kilogram of body weight. Ordinarily 0.5 to 50, and preferably 1 to 25 milligrams per kilogram per day given in divided doses 1 to 6 times a day or in sustained release form is effective to obtain desired results.

In general, the $sPLA_2$ inhibitor will be administered to a human so that a therapeutically effective amount is received. A therapeutically effective amount may coventionally be determined for an individual patient by administering the active compound in increasing doses and observing the effect on the patient.

Generally, the compound must be administered in a manner and a dose to achieve in the human a blood level concentration of $sPLA_2$ inhibitor of from 10 to 3000 nanograms/ml, and preferably a concentration of 100 to 800 nanograms/ml.

The treatment regimen may be from a single dose to multiple doses taken for years. Oral dosing is preferred for patient convenience and tolerance. With oral dosing, one to four oral doses per day, each from about 0.01 to 25 mg/kg of body weight with preferred doses being from about 0.1 mg/kg to about 2 mg/kg.

Parenteral administration (particularly, intravenous administration) is often preferred in instances where rapid alleviation of patient distress is required. With parenteral administration doses of 0.01 to 100 mg/kg/day administered continuously or intermittently throughout the day may be used. For parenteral administation, the compound may be administered in a physiologic saline vehicle (e.g., 0.9% normal saline, 0.45% normal saline, etc.) a dextrose vehicle (e.g., 5% dextrose in water), or a combination of saline and dextrose vehicle (0.9% normal saline in 5% dextrose).

Use and Proportion of Active Compound in the Method of the Invention

Another aspect of this invention is a method for treating septic shock, adult respiratory distress syndrome, pancreatitis, trauma, bronchial asthma, allergic rhinitis, rheumatoid arthritis, stroke, acute bronchitis, chronic bronchitis, acute bronchiolitis, chronic bronchiolitis, isteoarthritis, gout, spondylarthropathris, ankylosing spondylitis, Reiter's syndrome, psoriatic arthropathy, enterapathric spondylitis, juvenile arthropathy, juvenile ankylosing spondylitis, reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury, neuropathic joint disease (charco and joint), hemarthrosis (hemarthrosic), Henoch-Schonlein Purpura, hypertrophic osteoarthropathy, multicentric reticulohistiocytosis, surcoilosis, hemochromatosis, sickle cell disease and other hemoglobinopathries, hyperlipo proteineimia, hypogammaglobulinemia, hyperparathyroidism, acromegaly, familial Mediterranean fever, Behat's Disease, systemic lupus erythrematosis, hemophilia, relapsing polychondritis, and cystic fibrosis. The method comprises administering to a human having such diseases a therapeutically effective amount of the compound formula (I).

The compound of the invention, ((3-(2-amino-1,2-dioxoethyl)-1-((1,1'-biphenyl)-3-ylmethyl)-2-methyl-1H-indole-4-yl)oxy)acetic acid N,N-diethylglycolamido ester is believed to be a prodrug that transforms in the body of a mammal into ((3-(2-amino-1,2-dioxoethyl)-1-((1,1'-biphenyl)-3-ylmethyl)-2-methyl-1H-indol-4-yl)oxy)acetic acid. This acid is a known $sPLA_2$ inhibitor as shown by the following data (from U.S. Pat. No. 5,654,326):

Assay 1

A chromogenic assay procedure was used to evaluate ((3-(2-amino-1,2-dioxoethyl)-1-((1,1-biphenyl)-3-ylmethyl)-2-methyl-1H-indol-4-yl)oxy)acetic acid as an inhibitor of recombinant human secreted phospholipase $A_2$. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

TABLE I

| Compound of | Inhibition of human secreted $PLA_2$ $IC_{50}$ ± mean deviation (3–4 tests) |
|---|---|
| formula (II) | 4.33 ± 2.31 nM |

Conclusion: The compound of formula (II) is highly active in inhibiting $sPLA_2$.

Assay 2

A guinea pig lung tissue procedure was used evaluate ((3-(2-Amino-1,2-dioxoethyl)-1-((1,1'-biphenyl)-3-ylmethyl)-2-methyl-1H-indol-4-yl)oxy)acetic acid (compound of formula II) as an inhibitor of recombinant human secreted phospholipase $A_2$.

To estimate the drug-induced suppression of the maximal responses, $sPLA_2$ responses (10 ug/ml) were determined in the absence and presence of drug, and percent suppression was calculated for each pair of tissues.

Results of Human Secreted Phospholipase $A_2$ Inhibition Tests on Guinea Pig Lung Tissue

TABLE II

| Compound of | Tissue test secreted $PLA_2$ Apparent $K_B$nM |
|---|---|
| formula (II) | 57 ± 11 |

Assay III

The bioavailability of the compound of the invention, ((3-(2-amino-1,2-dioxoethyl)-1-((1,1'-biphenyl)-3-ylmethyl)-2-methyl-1H-indol-4-yl)oxy)acetic acid N,N-diethylglycolamido ester, was determined using a Rat Plasma Pharmacokinetics Study:

The purpose of this assay was to evaluate and compare the oral delivery for selected $sPLA_2$ inhibitors.

Test Subject
    Species: Rat
    Strain: Fischer 344
Dose Preparation
The amount of $sPLA_2$ inhibitor was corrected for free acid equivalents.
Vehicle
Suspension of $sPLA_2$ inhibitor in 10% Acacia, prepared just prior to dose administration
Dose Administration
Route: Oral
Frequency: Single dose
Dose: 10 mg/kg (of the parent acid)
Dosage Volume: 5 mL/kg
Rats fasted overnight.
Specimen Collection
Blood samples (0.8 ml) were obtained at the following times: 0.5, 1, 2, 4, 8 and 24 hours (2 rats/timepoint)
Data Analysis
Plasma was assayed by HPLC to measure concentrations of the different $sPLA_2$ inhibitors (as free acids).
Cmax (maximal plasma concentrations), and AUC values were determined from the mean plasma concentration-time profiles.

TABLE 3

| Compound ester type | Cmax (ng/ml) | AUC (0–8 hr) |
|---|---|---|
| morpholino-N-ethyl[1] | 1163 | 5192 |
| methyl[2] | 201 | 1129 |
| ethyl[3] | 56 | 241 |
| pivalate4[4] | 98 | 361 |
| isopropyl[5] | 491 | 2570 |
| N,N-diethylglycolamido[6] | 751 | 3398 |

[1]((3-(2-Amino-1,2-dioxoethyl)-1-((1,1'-biphenyl)-3-ylmethyl)-2-methyl-1H-indol-4-yl)oxy)acetic acid morpholino-N-ethyl ester (compound of the invention)
[2]((3-(2-Amino-1,2-dioxoethyl)-1-((1,1'-biphenyl)-3-ylmethyl)-2-methyl-1H-indol-4-yl)oxy)acetic acid methyl ester (this ester was evaluated in a separate study)
[3]((3-(2-Amino-1,2-dioxoethyl)-1-((1,1'-biphenyl)-3-ylmethyl)-2-methyl-1H-indol-4-yl)oxy)acetic acid ethyl ester
[4]((3-(2-Amino-1,2-dioxoethyl)-1-((1,1'-biphenyl)-3-ylmethyl)-2-methyl-1H-indol-4-yl)oxy)acetic acid pivalate ester
[5]((3-(2-Amino-1,2-dioxoethyl)-1-((1,1'-biphenyl)-3-ylmethyl)-2-methyl-1H-indol-4-yl)oxy)acetic acid isopropyl ester
[6]((3-(2-Amino-1,2-dioxoethyl)-1-((1,1'-biphenyl)-3-ylmethyl)-2-methyl-1H-indol-4-yl)oxy)acetic acid N,N-diethylglycolamido ester Table 3 shows that the N,N-diethylglycolamido ester, the compound of the invention is unexpectedly more bioavailable than many other esters of the $sPLA_2$ inhibitor, ((3-(2-Amino-1,2-dioxoethyl)-1-((1,1'-biphenyl)-3-ylmethyl)-2-methyl-1H-indol-4-yl)oxy)acetic acid.

While the present invention has been illustrated above by certain specific embodiments, it is not intended that these specific examples should limit the scope of the invention as described in the appended claims.

We claim:

1. The compound, ((3-(2-amino-1,2-dioxoethyl)-1-((1,1'-biphenyl)-3-ylmethyl)-2-methyl-1H-indol-4-yl)oxy)acetic acid N,N-diethylglycolamido ester.

2. A pharmaceutical formulation comprising the compound of claim 1 together with a pharmaceutically acceptable carrier or diluent therefor.

3. A method of inhibiting $sPLA_2$ mediated release of fatty acid which comprises contacting $sPLA_2$ with an therapeutically effective amount of the compound as claimed in claim 1.

4. The method of claim 3 wherein the contacting $sPLA_2$ is done by oral administration of the compound as claimed in claim 1.

5. Use of the 1H-indole-3-glyoxylamide compound represented by formula (I);

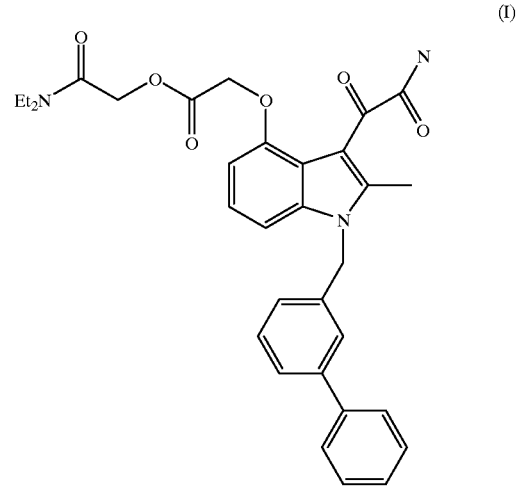

(I)

for the manufacture of a medicant for therapeutic treatment of septic shock, adult respiratory distress syndrome, pancreatitis, trauma, bronchial asthma, allergic rhinitis, rheumatoid arthritis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, juvenile arthropathy, juvenile ankylosing spondylitis, reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury, neuropathic joint disease (charco and joint), hemarthrosis (hemarthrosic), Henoch-Schonlein Purpura, hypertrophic osteoarthropathy, multicentric reticulohistiocytosis, surcoilosis, hemochromatosis, sickle cell disease and other hemoglobinopathries, hyperlipo proteineimia, hypogammaglobulinemia, hyperparathyroidism, acromegaly, familial Mediterranean fever, Behat's Disease, systemic lupus erythrematosis, hemophilia, relapsing polychondritis, and cystic fibrosis.

6. A method of treating a mammal, including a human, to alleviate the pathological effects of septic shock, adult respiratory distress syndrome, pancreatitis, trauma, bronchial asthma, allergic rhinitis, rheumatoid arthritis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, juvenile arthropathy, juvenile ankylosing spondylitis, reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury, neuropathic joint disease (charco and joint), hemarthrosis (hemarthrosic), Henoch-Schonlein Purpura, hypertrophic osteoarthropathy, multicentric reticulohistiocytosis, surcoilosis, hemochromatosis, sickle cell disease and other hemoglobinopathries, hyperlipo proteineimia, hypogammaglobulinemia, hyperparathyroidism, acromegaly, familial Mediterranean fever, Behat's Disease, systemic lupus erythrematosis, hemophilia, relapsing polychondritis, and cystic fibrosis; wherein the method comprises administering to said mammal a therapeutically effective amount of the compound as claimed in claim 1.

* * * * *